(12) United States Patent
Chen et al.

(10) Patent No.: US 10,611,713 B2
(45) Date of Patent: Apr. 7, 2020

(54) AUTOMATED PRODUCTION LINE FOR PREPARING CANNABIDIOL EXTRACT

(71) Applicant: Tianrui Chen, Beijing (CN)

(72) Inventors: Tianrui Chen, Beijing (CN); Luyi Peng, Beijing (CN); Rui Wang, Beijing (CN); Kai Chen, Beijing (CN)

(73) Assignee: Tianru Chen, Beijing (CN)

( * ) Notice: Subject to any disclaimer, the term of this patent is extended or adjusted under 35 U.S.C. 154(b) by 0 days.

(21) Appl. No.: 16/296,608

(22) Filed: Mar. 8, 2019

(65) Prior Publication Data

US 2019/0276384 A1 Sep. 12, 2019

(30) Foreign Application Priority Data

Mar. 9, 2018 (CN) .................... 2018 2 0330679 U
Mar. 5, 2019 (CA) ..................... 3035683

(51) Int. Cl.

| C07C 37/00 | (2006.01) |
| B01D 11/00 | (2006.01) |
| G05B 19/00 | (2006.01) |
| C07C 37/72 | (2006.01) |
| B01D 11/04 | (2006.01) |
| G05D 9/12 | (2006.01) |
| G05B 19/05 | (2006.01) |
| C07C 39/23 | (2006.01) |

(52) U.S. Cl.
CPC .......... *C07C 37/72* (2013.01); *B01D 11/0488* (2013.01); *B01D 11/0492* (2013.01); *C07C 37/004* (2013.01); *G05B 19/05* (2013.01); *G05D 9/12* (2013.01); *C07C 39/23* (2013.01)

(58) Field of Classification Search
CPC ..... C07C 37/72; C07C 37/004; B01D 11/049; G05B 19/05
See application file for complete search history.

(56) References Cited

U.S. PATENT DOCUMENTS

| 6,403,126 B1 | 6/2002 | Webster et al. |
| 10,155,176 B1 | 12/2018 | Feuer et al. |
| 2018/0147247 A1 | 5/2018 | Ivanov |

FOREIGN PATENT DOCUMENTS

| CA | 2391454 A1 | 12/2003 |
| CA | 2976004 A1 | 8/2016 |
| CN | 206244694 U | 6/2017 |
| CN | 107898826 A | 4/2018 |
| CN | 207591325 U | 7/2018 |
| WO | 2018/015886 A1 | 1/2018 |

*Primary Examiner* — Sikarl A Witherspoon
(74) *Attorney, Agent, or Firm* — Yong Chen; Lin Sun-Hoffman; Liu Chen & Hoffman LLP

(57) ABSTRACT

An automated production line for preparing cannabidiol (CBD) extracts is disclosed. The production line comprises sequentially a solvent dispensing tank, an extraction tank, a first concentration tank, a dilution tank, a filter, a second concentration tank, a chromatography column and a crystallization device. Each of these elements is connected to and controlled by a central controller. The controller can control the operation of these elements such that one element may operate independently of the other. Hence, each of these elements may operate for a sufficient period of time to allow the completion of the particular CBD production step carried out by that particular element. The amount of operations by humans may be reduced, thereby increasing the production efficiency.

19 Claims, 3 Drawing Sheets

AUTOMATED PRODUCTION LINE FOR PREPARING CANNABIDIOL EXTRACT

CROSS REFERENCE TO RELATED APPLICATION

This application claims the benefit of a Chinese Utility Model Patent Application No. 201820330679.4 entitled Fully Sealed Automated Production Line for Extracting Cannabidiol Extracts filed on Mar. 9, 2018 and a Canadian Patent Application No. 3,035,683 entitled Automated Production Line for Preparing Cannabidiol Extracts filed on Mar. 5, 2019, which are incorporated herein by reference as if fully set forth herein.

TECHNICAL FIELD

This disclosure relates generally to a system for preparing a cannabinoid extract from hemp and in particular, to an automated production line for preparing cannabidiol (CBD) extracts from industrial hemp.

BACKGROUND

Hemp (also referred to as industrial hemp) is primarily grown for industrial purposes and can be used to make a variety of commercial and industrial products including ropes, textiles, clothing, paper, food, bioplastics and insulation. Flowers, seeds, leaves, roots and stalks of hemp may be used as raw industrial materials.

Hemp and marijuana both derive from the *Cannabis Sativa* family. They share some similarities but also have crucial differences in their compositions. For example, when compared with marijuana, industrial hemp has a very low content (0.3% or less) of tetrahydrocannabinol (THC), which is known to induce psychoactive effects (i.e. getting a user "high"). In addition, hemp is abundant in CBD, a phenol substance, which decreases or eliminates the psychoactive effects of THC. Hence, CBD may be used for medicinal purposes, in skin products or as food or supplements to promote general health and well-being of a subject. At present, clinical research on CBD includes studies of anxiety, cognition, movement disorders and pains. It would be desirable to obtain CBD having a very low or no detectable THC content. However, current technologies for the production of CBD show a low production efficiency in this regard.

SUMMARY

An object of the present disclosure is to obtain a high efficiency in CBD production.

Accordingly, in one embodiment, the disclosure provides an automated production line for preparing CBD extracts from industrial hemp. The production line comprises a central controller, a solvent dispensing tank for preparing a separation solvent, an extraction tank containing flowers and leaves of the industrial hemp. The extraction tank is connected to the solvent dispensing tank via a first conduit equipped with a first solenoid valve and a first pump. Upon receiving a first activation signal from the central controller, the first solenoid valve and the first pump are activated to allow the separation solvent to follow through the first conduit into the extraction tank under the operation of the first pump to extract CBD from the flowers and leaves to form a CBD extract solution. The CBD extract solution then flows into a first concentration tank to be concentrated a first CBD concentrate. The first concentration tank is connected to the extraction tank via a second conduit equipped with a second solenoid valve and a second pump. Upon receiving a second activation signal from the central controller, the second solenoid valve and the second pump are activated to allow the CBD extract solution to follow through the second conduit into the first concentration tank under the operation of the second pump. The first CBD concentrate flows into a dilution tank to form a diluted CBD solution with a diluting solvent from a diluting solvent source. The dilution tank is connected to the first concentration tank via a third conduit equipped with a third solenoid valve and a third pump. Upon receiving a third activation signal from the central controller, the third solenoid valve and the third pump are activated to allow the first CBD concentrate to follow through the third conduit into the dilution tank under the operation of the third pump. The diluted CBD solution then flows to a filter press to be filtered to form a CBD filtrate. The filter press is connected to the dilution tank via a fourth conduit equipped with a fourth solenoid valve and a fourth pump. Upon receiving a fourth activation signal from the central controller, the fourth solenoid valve and the fourth pump are activated to allow the diluted CBD solution to follow through the fourth conduit to the filter press under the operation of the fourth pump. The CBD filtrate then flows into a second concentration tank to be concentrated to form a second CBD concentrate. The second concentration tank is connected to the filter press via a fifth conduit equipped with a fifth solenoid valve and a fifth pump. Upon receiving a fifth activation signal from the central controller, the fifth solenoid valve and the fifth valve are activated to allow the CBD filtrate to follow through the fifth conduit into the second concentration tank under the operation of the fifth pump. The second CBD concentrate is loaded onto a chromatography column to form a CBD eluate. The chromatography column also receives an eluent from an eluent source. The eluent elutes the second CBD concentrate to form the CBD eluate. The chromatography column is connected to the second concentration tank via a sixth conduit equipped with a sixth solenoid valve and a sixth pump. Upon receiving a sixth signal from the central controller, the sixth solenoid valve and the sixth valve are activated to allow the second CBD concentrate to flow through the sixth conduit under the operation of the sixth pump to be loaded onto the chromatography column. A crystallization device then receives and crystalizes the CBD eluate to yield the CBD extracts. The crystallization device is connected to the chromatography column via a seventh conduit equipped with a seventh solenoid valve and a seventh pump. Upon receiving a seventh activation signal from the central controller, the seventh solenoid valve and the seventh pump are activated to allow the CBD eluate to follow through the seventh conduit into the crystallization device under the operation of the seventh pump.

The automated CBD production line of the present disclosure may extract CBD from flowers and leaves of industrial hemp with efficiency. In one embodiment, the production of CBD extracts from flowers and leaves of industrial hemp may be completed through a cycle of initial crude purification or extraction, a first concentration, dilution, filtration, a second concentration, elution by column chromatography and crystallization. The purity of CBD extracts thus obtained may be enhanced upon the completion of the cycle.

In one embodiment, the CBD production line is controlled by a central controller, which may minimize the amount of operations by humans, thereby increasing the production efficiency.

In one embodiment, the level of the separation solvent in the solvent dispensing tank may be displayed by a solvent level indication system coupled thereto. When the level of the separation solvent is below a first pre-set solvent level, a first solvent level indicator may issue a warning. When the level of the separation solvent is below a second pre-set solvent level, a second solvent level indicator may issue a warning. Hence, an operator may act accordingly to adjust the level of the separation solvent in the solvent dispensing tank.

BRIEF DESCRIPTION OF THE DRAWINGS

An embodiment will now be described in detail by way of example, with reference to the accompanying drawings in which.

Figure 1:
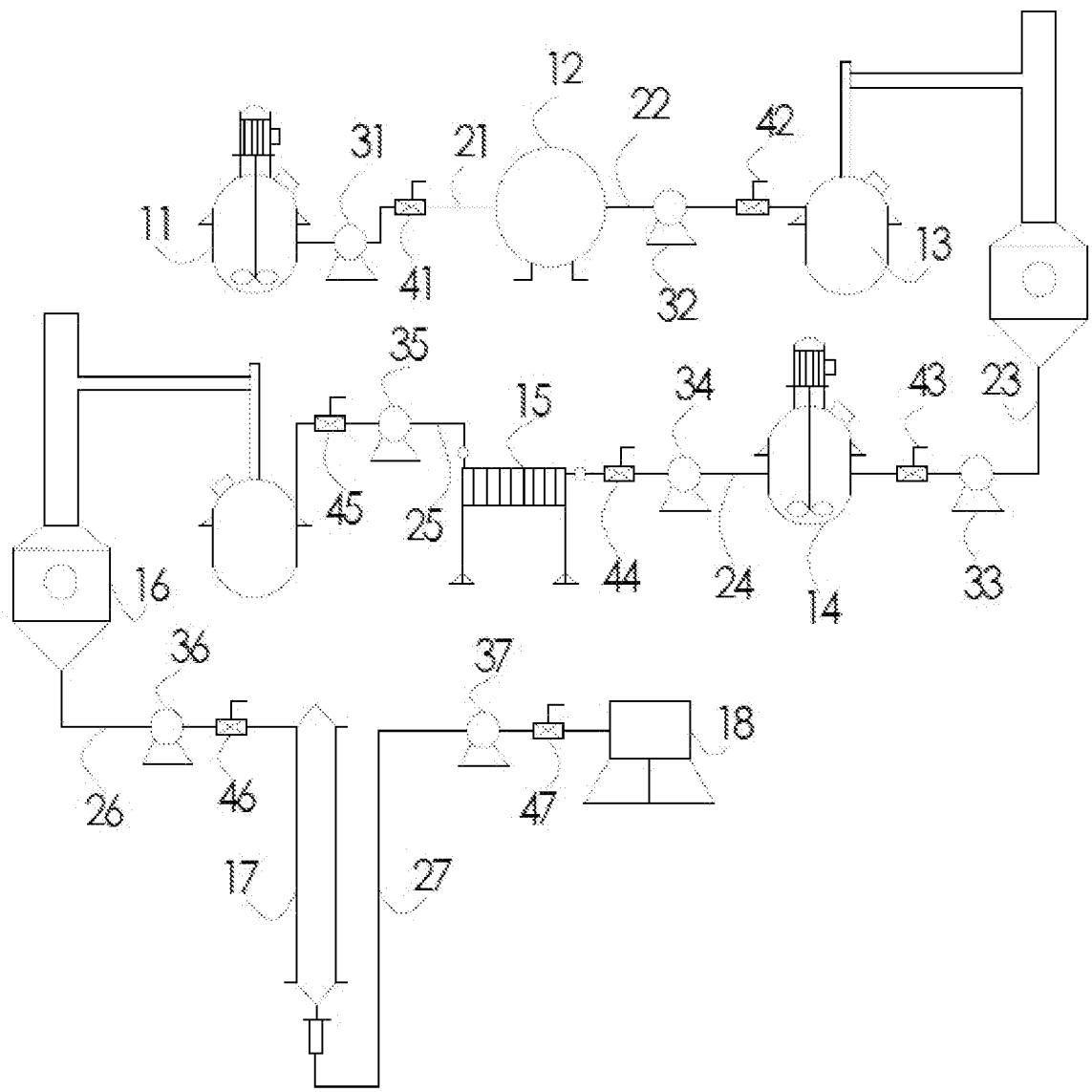
FIG. 1 is a diagram showing an automated production line for preparing CBD extracts from industrial hemp in accordance with one embodiment of the present disclosure.
Figure 2:
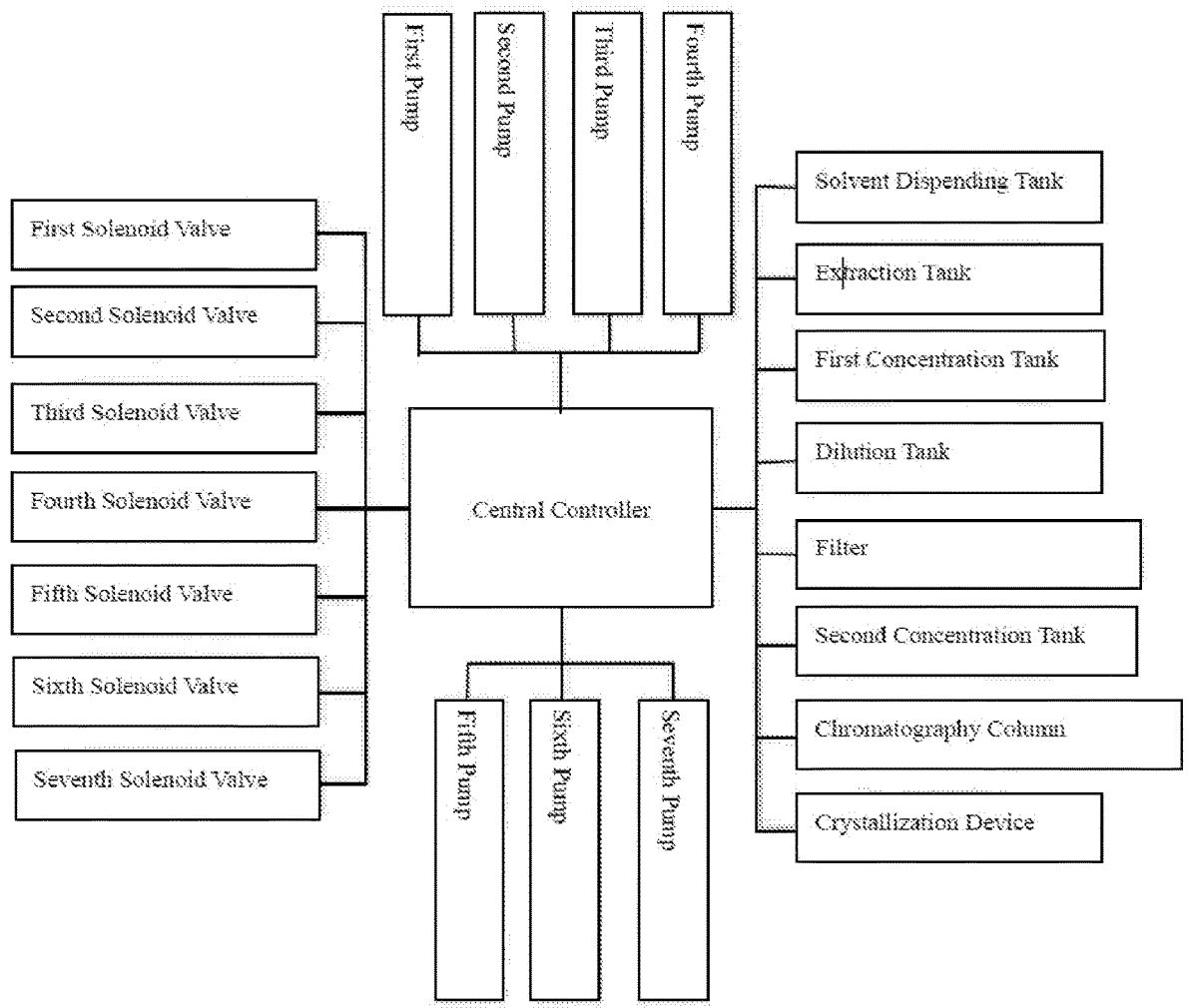
FIG. 2 is a schematic diagram illustrating the connection of various elements to the central controller of the automated production line of FIG. 1.
Figure 3:
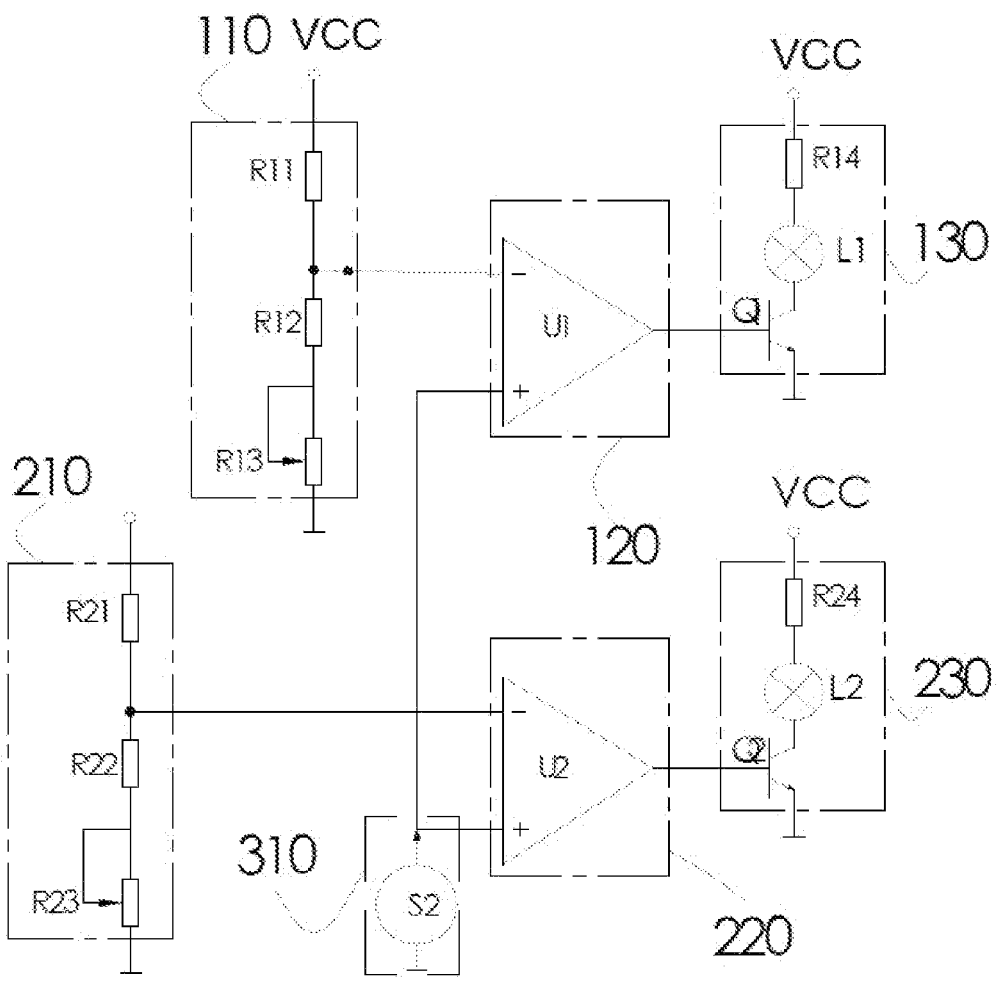
FIG. 3 is a schematic diagram of the solvent level indication system provided to the solvent dispensing tank of the automated production line of FIG. 1.

The following components or elements are shown in FIGS. 1-3: (11) solvent dispensing tank; (12) extraction tank; (13) first concentration tank; (14) dilution tank; (15) filter; (16) second concentration tank; (17) chromatography column; (18) crystallization device; (19) central controller; (21) first conduit; (22) second conduit; (23) third conduit; (24) fourth conduit; (25) fifth conduit; (26) sixth conduit; (27) seventh conduit; (31) first pump; (32) second pump; (33) third pump; (34) fourth pump; (35) fifth pump; (36) sixth pump; (37) seventh pump; (41) first solenoid valve; (42) second solenoid valve; (43) third solenoid valve; (44) fourth solenoid valve; (45) fifth solenoid valve; (46) sixth solenoid valve; (47) seventh solenoid valve; (110) first reference device; (120) first comparison device; (130) first indicator; (210) second reference device; (220) second comparison device; (230) second indicator; (310) solvent level sensor; (R11) first reference resistor; (R12) second reference resistor; (R13) third reference resistor; (R21) fourth reference resistor; (R22) fifth reference resistor; (R23) sixth reference resistor; (R14) first resistor; (R24) second resistor; (U1) first rectifier; (U2) second rectifier; (L1) first light; (L2) second light; (S2) pump; (Q1) first switch and (Q2) second switch.

DETAILED DESCRIPTION

The description, which follows, and the embodiments described therein, are provided by way of illustration of an example, or examples of particular embodiments of principles and aspects of the present invention. These examples are provided for the purposes of explanation, and not of limitation, of those principles and of the invention. In the description that follows, like parts are marked throughout the specification and the drawings with the same respective reference numerals.

Directional or positional terms "central", "up", "down", "left", "right", "vertical", "horizontal", "inner" and "outer" refer to the directions or positions shown in the drawings and are not intended to be limiting and should not be interpreted as limitations. Terms such as "first", "second" and the like are for illustration only and should not be interpreted as indicating or implying the relative significance of the elements.

Referring to FIGS. 1 and 2, an exemplary automated production line for preparing CBD extracts from industrial hemp is shown. The production comprises a central controller 19. As further explained below, the central controller is connected electronically to the other components of the production line. The controller receives inputs from the other components and accordingly sends out command signals to activate a series of solenoid valves that are equipped on a series of conduits in order to carry out the steps for producing the CBD extracts. In some embodiments, the central controller may be a computer terminal or a programmable logic controller.

As shown in FIG. 1, the exemplary production line comprises a solvent dispensing tank 11 for preparing and dispensing a separation solvent. The separation solvent can be an organic solvent. Exemplary organic solvents may be n-hexane, dichloromethane, petroleum ether, ethyl acetate, ethanol or methanol or any combinations thereof.

Crude Purification/Extraction

The solvent dispensing tank 11 is connected to an extraction tank 12 containing hemp flowers and leaves of the industrial tank via a first conduit 21. The solvent dispensing tank 11 dispenses the separation solvent into the extraction tank 12 through the first conduit 21. The first conduit 21 is provided with a first solenoid valve 41 and a first pump 31, which control and facilitate the flow of the separation solvent from the solvent dispensing tank 11 to the extraction tank 12. In one embodiment, the first solenoid valve 41 and the first pump 31 receive a first activation signal from the central controller 19 after a first pre-set time interval is reached. The first solenoid valve 41 and the first pump 31 are then activated to allow the follow of the separation solvent into the extraction tank 12 through the first conduit 21 by the use of the first pump 31. In another embodiment, the first pump 31 may be activated by the first solenoid valve 41.

Inside the exaction tank 12, an initial crude purification of the hemp flowers and leaves is carried out. The separation solvent sufficiently mixes with the flowers and leaves. The mixture is then extracted by the use of the separation solvent to form a CBD extract solution, which is a slurry containing the hemp flowers and leaves and CBD dissolved in the separation solvent.

First Concentration

The first concentration tank 13 is connected to the extraction tank 12 via a second conduit 22. The second conduit 22 is provided with a second solenoid valve 42 and a second pump 32, which control and facilitate the flow of the CBD extract solution from the extraction tank 12 to the first concentration tank 13. The second solenoid valve 42 and the second pump 32 may control and facilitate the flow of the CBD extract solution in a similar fashion as the first solenoid valve 41 and the first pump 31. In one embodiment, the second solenoid valve 42 and the second pump 32 are activated upon receiving a second activation signal from the central controller 19. It is also possible that the second pump 32 is activated by the second solenoid valve 42. The central controller 19 sends out the second activation signal when it receives a first CBD content input indicating that the CBD content of the CBD extract solution has reached a pre-determined value. The CBD content of the CBD extract solution may be determined by sampling the solution periodically and measure the CBD content of the sample for example by a conventional instrument such as chromatography. For example, a high performance liquid chromatography instrument may be used.

Inside the first concentration tank 13, a first concentration step is carried out and the CBD extract solution is concentrated to form a first CBD concentrate. As would be appreciated by a person of ordinary skill in the art, any commonly used concentration method may be used. For example, the CBD extract solution may be concentrated by distillation to form the first CBD concentrate. The first CBD concentrate is a slurry of the hemp flowers and leaves with CBD dissolved in a reduced volume of the separation solvent.

Dilution

A dilution tank 14 is connected to the first concentration tank 13 via a third conduit 23. The third conduit 23 is provided with a third solenoid valve 43 and a third pump 33, which control and facilitate the flow of the first CBD concentrate from the first concentration tank 13 to the dilution tank 14. The third solenoid valve 43 and the third pump 33 may control and facilitate the flow of the first CBD concentrate in a similar fashion as the first solenoid valve 41 and the first pump 31. In one embodiment, the third solenoid valve 43 and the third pump 33 are activated upon receiving a third activation signal from the central controller 19. In another embodiment, the third pump 33 may be activated by the third solenoid valve 43. The central controller 19 sends out the third activation signal when a second pre-set time interval is reached. The second pre-set time interval may correspond to the time period required for completing the first concentration step in the first concentration tank 13.

Inside the dilution tank 14, the first CBD concentrate is further dissolved and diluted with a suitable organic solvent to form a diluted CBD solution. The diluted CBD solution is a slurry containing the hemp flowers and leaves with CBD dissolved in a large volume of the organic solvent.

In some embodiments, the dilution tank 14 is connected to a diluting solvent source which supplies the diluting solvent to the dilution tank 14.

Filtration

A filter press 15 is connected to the dilution tank 14 via a fourth conduit 24. In some embodiments, the filter press may be a plate and frame filter press or a membrane filter press. The membrane filter may be a 0.2 nm membrane filter.

The fourth conduit 24 is provided with a fourth solenoid valve 44 and a fourth pump 34, which control and facilitate the flow of the diluted CBD solution from the dilution tank 14 to the filter press 15. The fourth solenoid valve 44 and the fourth pump 34 may control and facilitate the flow of the diluted CBD solution in a similar fashion as the first solenoid valve 41 and the first pump 31. In one embodiment, the central controller 19 sends a fourth activation signal to the fourth solenoid valve 44 and/or the four pump 34 after a pre-determined volume of the diluting solvent has been dispensed. The pre-determined volume of the diluting solvent may be measured by a sensing means coupled to the dilution tank 14. The sensing means may measure the level of the diluting solvent in the dilution tank 14, the flow volume of the diluting solvent, or both. In another embodiment, the fourth pump may be activated by the fourth solenoid valve.

The diluted CBD solution filters through the filter press 15 to remove solid impurities contained in the diluted CBD solution, for example, the hemp flowers and leaves, and to form a CBD filtrate.

Second Concentration

A second concentration tank 16 is connected to the filter press 15 through a fifth conduit 25. The fifth conduit 25 is provided with a fifth solenoid valve 45 and a fifth pump 35, which control and facilitate the flow of the CBD filtrate from the filter press 15 to the second concentration tank 16. The fifth solenoid valve 45 and the fifth pump 35 may control and facilitate the flow of the CBD filtrate in a similar fashion as the first solenoid valve 41 and the first pump 31. In one embodiment, the fifth conduit is also equipped with a sensor. The sensor measures whether a pre-determined flow pressure, or a pre-determined flow solvent level or both has been reached. Once the pre-determined values have been reached, the sensor sends an input to the central controller 19. Upon receiving the input from the sensor, the central controller 19 activates the fifth solenoid valve 45 and the fifth pump 35 by sending a fifth activation signal to it. The activation of the fifth solenoid valve 45 allows the flow of the CBD filtrate to the second concentration tank 16 under the operation of the fifth pump 35. In another embodiment, the fifth pump may be activated by the fifth solenoid valve.

Inside the second concentration tank 16, a second concentration treatment is carried out, resulting in the formation of a second CBD concentrate with little or no impurities. The impurities may include cannabinol (CBN) and chlorophyll.

Elution

A chromatography column 17 for example packed with silica is connected to the second concentration tank 16 via a sixth conduit 26. The chromatography column 17 may be connected with an eluent source to dispense an eluent to the chromatography column 17 to elute the second CBD concentrate.

The sixth conduit 26 is provided with a sixth solenoid valve 46 and a sixth pump 36, which control and facilitate the flow of the second CBD concentrate from the second concentration tank 16 to the chromatography column 17. The sixth solenoid valve 46 and the sixth pump 36 may control and facilitate the flow of the second CBD concentrate in a similar fashion as the first solenoid valve 41 and the first pump 31. In one embodiment, the central controller 19 sends a sixth activation signal to the sixth solenoid valve 46 and/or the sixth pump 36 to activate these elements after a second pre-determined time interval has lapsed.

Through the chromatography column 17, the second CBD concentrate is separated and eluted to form an eluate that contains essentially only CBD. The chromatography column 17 is linked to a HPLC that analyzes the eluate to determine which portion of the eluate contains only CBD.

Crystallization

A crystallization device 18 is connected to the chromatography column 17 via a seventh conduit 27. A commercially available crystallizer, for example, a batch vacuum crystallizer, may be used. Through the crystallization device 18, the CBD eluate crystallizes into crystallized CBD extracts. The crystallized CBD extracts may be free of any detectable amount of THC.

The seventh conduit 27 is provided with a seventh solenoid valve 47 and a seventh pump 37, which control and facilitate the flow of the second CBD concentrate from the chromatography column 17 to the crystallization device 18. The seventh solenoid valve 47 and the seventh pump 37 may control and facilitate the flow in a similar fashion as the first solenoid valve 41 and the first pump 31. In one embodiment, when the HPLC connected to the chromatography column 17 detects only CBD in the eluate, it sends a second CBD content input to the central controller 19. The central controller 19 then sends a seventh activation signal to activate the seventh solenoid valve 47 and/or the seventh pump 37. The seventh pump 37 may also be activated by the seventh solenoid valve 47. Upon activation of the seventh solenoid valve 47 and the seventh pump 37, the second CBD concentrate flows into the crystallization device under the operation of the seventh pump 37 to be crystalized into the CBD extracts.

In some embodiments, the first to the seventh solenoid valves may be the same or different. As would be appreciated by a person of ordinary skilled in the art, a solenoid valve is a electromechanical device in which the solenoid uses an electric current to generate a magnetic field and thereby operate a mechanism which regulates the opening of fluid flow in a valve. Therefore, any solenoid valves that are commonly used to shut off, release, dose, distribute or mix fluids (liquids or slurries) may be used.

In some embodiments, the first to the seventh pumps may be the same or different. Any pumps that are capable of moving fluids may be suitable. For example, a suitable pump may be a positive displacement pump such as a peristaltic pump. According to one embodiment, the flow rate of a fluid in the production line may be controlled by a frequency converter coupled to the pump. The frequency convertor controls the output power of the pump, thereby controlling the flow rate of the fluid.

In one embodiment, as illustrated in FIG. 2, the solvent dispensing tank 11, the extraction tank 12, the first concentration tank 13, the dilution tank 14, the filter press 15, the second concentration tank 16, the chromatography column 17 and the crystallization device 18 may be connected to and controlled by the central controller 19. The controller can control the operation of these elements such that one element may operate independently of the other. In this way, each of these elements may operate for a sufficient period of time to allow the completion of the particular CBD production step carried out by that particular element.

In one embodiment, the first electric to the seventh solenoid valves and the first to the seventh pumps may also be connected to and controlled by the central controller 19. The controller can control the solenoid valves and the pumps to facilitate the flow of the materials from one element to the next element depending on the particular CBD production step.

Through the use of a central controller, the production line may be operated with a significant degree of automation. This may allow a continuous operation of the production line, thereby increasing the efficiency to produce the CBD extracts. A further benefit may be that it would be safer to operate the production line without much human intervention.

In one embodiment, the chromatography column 17 is connected to an eluent inlet pipe connected to an eluent source for injecting an eluent to the column. The eluent elutes the second CBD concentrate to produce an eluate containing only CBD.

In another embodiment, the dilution tank 14 is connected to a diluting solvent inlet pipe connected to a diluting solvent source for injecting the diluting solvent into the dilution tank 14.

In a further embodiment, as illustrated in FIG. 3, the solvent dispensing tank 11 is provided with a solvent level indication system. The system comprises a solvent level sensor 310 to detect the solvent level in the dispensing tank 11 and calculate a voltage based on the detected solvent level.

The solvent level sensor 310 comprises a pump S2.

A first reference device 110 generates a first reference voltage based on a first pre-set solvent level in the solvent dispensing tank 11. The first reference device 110 comprises a first (R11), a second (R12) and a third (R13) reference resistors connected in series to ground. The first and the second reference resistors are coupled to a first comparison device 120, which may comprise for example, a first rectifier U1. The first reference voltage is generated based on a division of the voltage among the first to the third reference resistors.

A second reference device 210 generates a second reference voltage based on a second pre-set solvent level in the solvent dispensing tank 1. The second reference device 210 comprises a fourth (R21), a fifth (R22) and a sixth (R23) reference resistors connected in series to ground. The fourth and the fifth reference resistors are coupled to a second comparison device 220, which may comprise for example, a second rectifier U2. The second reference voltage is generated based on a division of the voltage among the fourth to the sixth reference resistors.

The first comparison device 120 is coupled to the solvent level sensor 310 and the first reference device 110. It outputs a first drive command when the measured voltage is greater than the first reference voltage. In one embodiment, the first comparison device 120 may be a voltage comparator. The solvent level sensor 310 couples with the positive input end of the first comparison device 120 and the first reference device 110 couples with the negative input end of the first comparison device 120.

A second comparison device 220 is coupled to the solvent level sensor 310 and the second reference device 210. The second comparison device 220 outputs a second drive command when the measured voltage is greater than the second reference voltage. In one embodiment, the second comparison device 220 may be a voltage comparator. The solvent level sensor 310 couples with the positive input end of the voltage comparator of the second comparison device 220 and the second reference device 210 couples with the negative input end.

In one embodiment, a first indication device 130 is coupled to the first comparison device 120 and operated by the first drive command generated by the first comparison device 120. The first indication device 130 may comprise a first light L1 connected with a first resistor R14 and a first switch Q1. The first drive command turns on the first switch Q1 which then turns on the first light L1. A second indication device 230 is coupled to the second comparison device 220 and operated by the second drive command generated by the second comparison device 220. The second indication device may comprise a second light L2, a second resistor R24 and a second switch Q2. The second drive command turns on the second switch Q2 which then turns on the second light L2.

While the principles of the invention have been shown and described in connection with specific embodiments, it is to be understood that such embodiments are by way of example and are not limiting. As is evident from the foregoing description, certain aspects of the present invention are not limited by the particular details of the invention illustrated in the drawings. Other modifications and applications, or equivalents, will occur to those skilled in the art. The terms "having", "comprising" and "including" and similar terms as used in the foregoing specification are used in the sense of "optional" or "may include" and not as "required". Many changes, modifications, variations and other uses and applications of the present construction will, however, become apparent to those skilled in the art after considering the specification and attached drawings. All such changes, modifications, variations and other uses and applications which do not depart from the spirit and scope of the invention are deemed to be covered by the invention which is limited only by the claims that follow. The scope of the disclosure is not intended to be limited to the embodiments shown herein, but is to be accorded the full scope consistent with the claims, wherein reference to an element in the singular is not intended to mean "one and only one" unless specifically so stated, but rather one or more.

The invention claimed is:

1. An automated production line for preparing cannabidiol (CBD) extracts from industrial hemp, the production line comprising:
    a central controller;
    a solvent dispensing tank for preparing a separation solvent;
    an extraction tank containing flowers and leaves of the industrial hemp, the extraction tank being connected to the solvent dispensing tank via a first conduit equipped with a first solenoid valve and a first pump, wherein upon receiving a first activation signal from the central controller, the first solenoid valve and the first pump activated to allow the separation solvent to follow through the first conduit into the extraction tank under the operation of the first pump to extract CBD from the flowers and leaves to form a CBD extract solution;
    a first concentration tank to receive and concentrate the CBD extract solution to form a first CBD concentrate, the first concentration tank being connected to the extraction tank via a second conduit equipped with a second solenoid valve and a second pump, wherein upon receiving a second activation signal from the central controller, the second solenoid valve and the second pump are activated to allow the CBD extract solution to follow through the second conduit into the first concentration tank under the operation of the second pump;
    a dilution tank to receive a diluting solvent from a diluting solvent source and the first CBD concentrate to dilute the first CBD concentrate with the diluting solvent into a diluted CBD solution, the dilution tank being connected to the first concentration tank via a third conduit equipped with a third solenoid valve and a third pump, wherein upon receiving a third activation signal from the central controller, the third solenoid valve and the third pump are activated to allow the first CBD concentrate to follow through the third conduit into the dilution tank under the operation of the third pump;
    a filter press to filer the diluted CBD solution to form a CBD filtrate, the filter press being connected to the dilution tank via a fourth conduit equipped with a fourth solenoid valve and a fourth pump, wherein upon receiving a fourth activation signal from the central controller, the fourth solenoid valve and the fourth pump are activated to allow the diluted CBD solution to follow through the fourth conduit to the filter press under the operation of the fourth pump;
    a second concentration tank to receive and concentrate the CBD filtrate to form a second CBD concentrate, the second concentration tank being connected to the filter press via a fifth conduit equipped with a fifth solenoid valve and a fifth pump, wherein upon receiving a fifth activation signal from the central controller, the fifth solenoid valve and the fifth valve are activated to allow the CBD filtrate to follow through the fifth conduit into the second concentration tank under the operation of the fifth pump;
    a chromatography column to receive an eluent from an eluent source and the second CBD concentrate, wherein the eluent elutes the second CBD concentrate to form a CBD eluate, the chromatography column being connected to the second concentration tank via a sixth conduit equipped with a sixth solenoid valve and a sixth pump, wherein upon receiving a sixth signal from the central controller, the sixth solenoid valve and the sixth valve are activated to allow the second CBD concentrate to flow through the sixth conduit under the operation of the sixth pump to be loaded onto the chromatography column; and
    a crystallization device to receive and crystalize the CBD eluate to obtain the CBD extracts, the crystallization device being connected to the chromatography column via a seventh conduit equipped with a seventh solenoid valve and a seventh pump, wherein upon receiving a seventh activation signal from the central controller, the seventh solenoid valve and the seventh pump are activated to allow the CBD eluate to follow through the seventh conduit into the crystallization device under the operation of the seventh pump.

2. The automated production line of claim 1, wherein the fifth conduit further comprises a sensor.

3. The automated production line of claim 1, wherein the central controller sends the first activation signal to the first solenoid valve and the first pump when a first pre-set time interval is reached.

4. The automated production line of claim 1, wherein the central controller sends the second activation signal to the second solenoid valve and the second pump when it receives a first CBD content input that the CBD extract solution has reached a pre-determined CBD content.

5. The automated production line of claim 1, wherein the central controller sends the third activation signal to the third solenoid valve and the third pump when a second pre-set time interval is reached.

6. The automated production line of claim 1, wherein the central controller sends the fourth activation signal to the fourth solenoid valve and the fourth pump when a pre-determined volume of the diluting solvent has been dispensed.

7. The automated production line of claim 1, wherein the central controller sends the fifth activation signal to the fifth solenoid valve and the fifth pump when it receives an input from the sensor that the filtration has been completed.

8. The automated production line of claim 1, wherein the central controller sends the sixth activation signal to the sixth solenoid valve and the seventh pump when a third pre-set time interval is reached.

9. The automated production line of claim 1, wherein the central controller sends the seventh activation signal to the seventh solenoid when it receives a second CBD content input that only CBD is detected by a HPLC connected to the chromatography column.

10. The automated production line of claim 1, wherein the first to the seventh pumps are peristaltic pumps.

11. The automated production line of claim 1, wherein the filter press is a plate and frame filter press or a membrane filer press.

12. The automated production line of claim 4, wherein a sample of the CBD extract solution is taken and analyzed periodically to determine whether the CBD extract solution has reached the pre-determined CBD content.

13. The automated production line of claim 1, wherein the central controller is a computer.

14. The automated production line of claim 1, wherein the central controller is a programmable logic controller.

15. The automated production line claim 6, wherein the solvent dispensing tank is provided with a solvent level indication system, the system comprising a solvent level sensor to detect a solvent level in the solvent dispensing tank and measure a voltage based on the detected solvent level;

a first reference device to generate a first reference voltage based on a first pre-set solvent level in the solvent dispensing tank;

a second reference device to generate a second reference voltage based on a second pre-set solvent level in the solvent dispensing tank;

a first comparison device coupled to the solvent level sensor and the first reference device, wherein the first comparison device outputs a first drive command when the measured voltage is greater than the first reference voltage;

a second comparison device coupled to the solvent level sensor and the second reference device, wherein the second comparison device outputs a second drive command when the measured voltage is greater than the second reference voltage;

a first operation device coupled to the first comparison device, the first operation device being triggered by the first drive command; and a second operation device coupled to the second comparison device, the second operation device being triggered by the second drive command.

16. The automated production line of claim 15, wherein the first reference device comprises a first, a second and a third reference resistors connected in series to ground, wherein the first and the second reference resistors are coupled to the first comparison device.

17. The automated production line of claim 15, wherein the second reference device comprises a fourth, a fifth and a sixth reference resistors connected in series to ground, wherein the fourth and the fifth reference resistors are coupled to the second comparison device.

18. The automated production line of claim 15, wherein the first and the second comparison devices are voltage comparators.

19. The automated production line of claim 2, wherein the sensor detects a flow pressure, a flow solvent level or both.

\* \* \* \* \*